United States Patent
Van Der Heide

(10) Patent No.: US 10,647,646 B2
(45) Date of Patent: May 12, 2020

(54) PROCESS FOR THE PRODUCTION OF GLYCOLS

(71) Applicant: SHELL OIL COMPANY, Houston, TX (US)

(72) Inventor: Evert Van Der Heide, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/344,850

(22) PCT Filed: Oct. 25, 2017

(86) PCT No.: PCT/EP2017/077360
§ 371 (c)(1),
(2) Date: Apr. 25, 2019

(87) PCT Pub. No.: WO2018/077979
PCT Pub. Date: May 3, 2018

(65) Prior Publication Data
US 2020/0048172 A1 Feb. 13, 2020

(30) Foreign Application Priority Data
Oct. 28, 2016 (EP) .................................... 16196423

(51) Int. Cl.
*C07C 29/132* (2006.01)
*B01J 23/30* (2006.01)
(Continued)

(52) U.S. Cl.
CPC ............. *C07C 29/132* (2013.01); *B01J 23/10* (2013.01); *B01J 23/14* (2013.01); *B01J 23/28* (2013.01);
(Continued)

(58) Field of Classification Search
CPC ...... C07C 31/202; C07C 29/60; C07C 31/205; B01J 29/132; B01J 23/14; B01J 23/745;
(Continued)

(56) References Cited

U.S. PATENT DOCUMENTS

2016/0145178 A1    5/2016   Kalnes et al.

FOREIGN PATENT DOCUMENTS

| WO | 2015028398 A1 | 3/2015 |
| WO | 2015154258 A1 | 10/2015 |

OTHER PUBLICATIONS

International Search Report and Written Opinion received for PCT Patent Application No. PCT/EP2017/077360, dated Jan. 30, 2018, 8 pages.

(Continued)

*Primary Examiner* — Jafar F Parsa

(57) ABSTRACT

A process for the production of glycols is provided, the process comprising the steps of: (i) contacting a saccharide-containing feedstock with a catalyst system in a reactor in the presence of a reaction medium, a buffer system for controlling the pH within the reactor, and hydrogen; (ii) withdrawing a reactor product stream from the reactor; (iii) separating the reactor product stream into at least a glycol product stream and a hydrocarbon heavies stream; and (iv) recycling the hydrocarbon heavies stream at least partially back to the reactor; wherein components of the buffer system withdrawn from the reactor in the reactor product stream separate with the heavies stream and are recycled therewith.

10 Claims, 1 Drawing Sheet

(51) Int. Cl.
*B01J 23/28* (2006.01)
*B01J 23/10* (2006.01)
*B01J 23/14* (2006.01)
*B01J 23/745* (2006.01)
*B01J 23/46* (2006.01)
*B01J 23/755* (2006.01)
*B01J 23/44* (2006.01)
*B01J 23/42* (2006.01)
*B01J 23/75* (2006.01)

(52) U.S. Cl.
CPC ............... *B01J 23/30* (2013.01); *B01J 23/42* (2013.01); *B01J 23/44* (2013.01); *B01J 23/462* (2013.01); *B01J 23/464* (2013.01); *B01J 23/468* (2013.01); *B01J 23/745* (2013.01); *B01J 23/75* (2013.01); *B01J 23/755* (2013.01)

(58) Field of Classification Search
CPC . B01J 23/42; B01J 23/28; B01J 23/462; B01J 23/755; B01J 23/44; B01J 23/75; B01J 23/468; B01J 23/464; B01J 23/10; B01J 23/30
See application file for complete search history.

(56) References Cited

OTHER PUBLICATIONS

Ji et al, "Direct Catalytic Conversion of Cellulose into Ethylene Glycol Using Nickel-Promoted Tungsten Carbide Catalysts", Angewandte Chemie International Edition, vol. 47, Issue No. 44, Oct. 20, 2008, pp. 8510-8513.

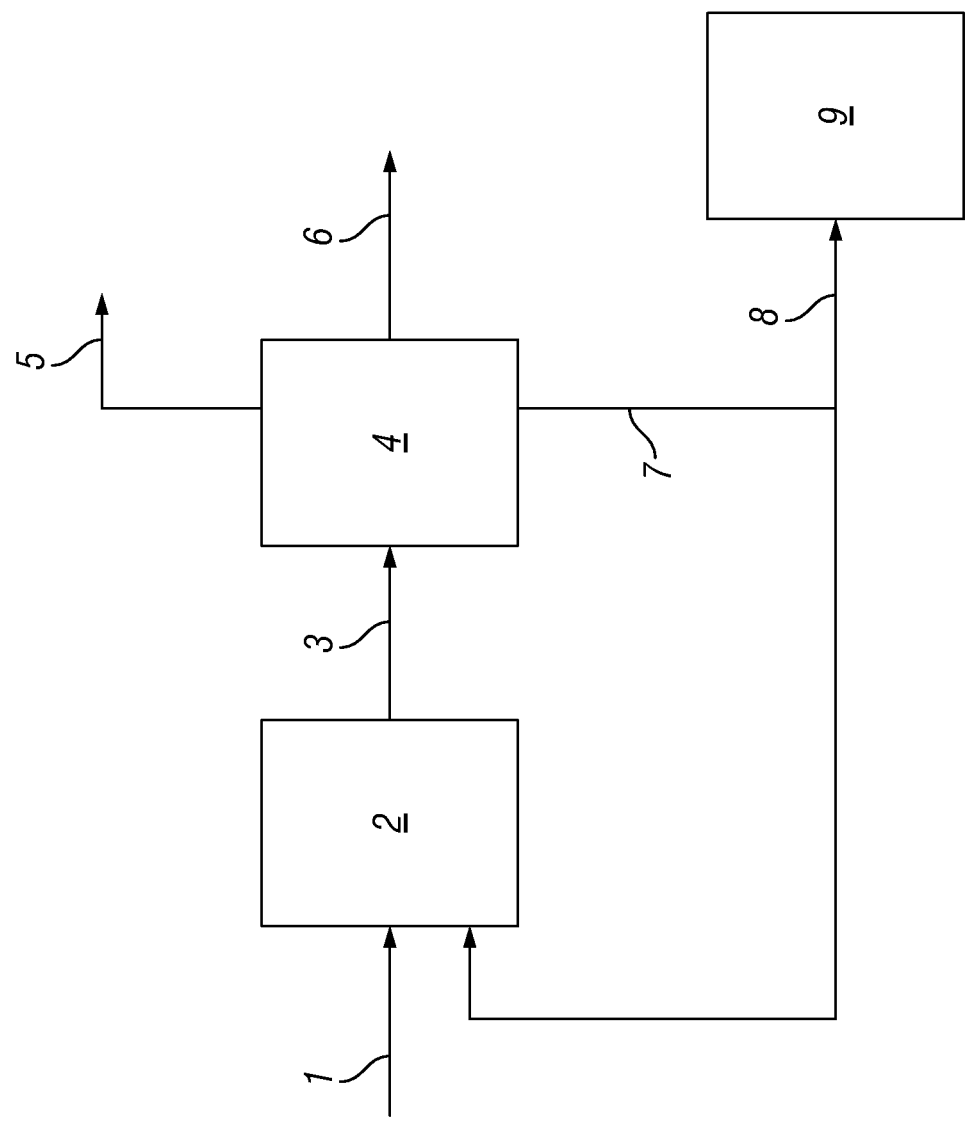

PROCESS FOR THE PRODUCTION OF GLYCOLS

CROSS REFERENCE TO RELATED APPLICATIONS

This is a national stage application of International Application No. PCT/EP2017/077360, filed 25 Oct. 2017, which claims benefit of priority to European Patent Application No. 16196423.4, filed 28 Oct. 2016.

FIELD OF THE INVENTION

The present invention relates to a process for preparing glycols from a saccharide-containing feedstock.

BACKGROUND

Ethylene glycol and propylene glycol are valuable materials with a multitude of commercial applications, e.g. as heat transfer media, antifreeze, and precursors to polymers, such as PET. Historically, ethylene and propylene glycols have been made on an industrial scale by hydrolysis of the corresponding alkylene oxides, which are the oxidation products of ethylene and propylene, produced from fossil fuels.

More recently, efforts have focused on producing chemicals, including glycols, from renewable feedstocks, such as sugar-based materials. The conversion of sugars to glycols offers an efficient use of the starting materials with the oxygen atoms remaining intact in the desired product.

Current methods for the conversion of saccharides to sugars revolve around a hydrogenation/hydrogenolysis process as described in Angew. Chem. Int. Ed. 2008, 47, 8510-8513.

WO 2015/028398 describes a continuous process for the conversion of a saccharide-containing feedstock into glycols. In this process the saccharide-containing feedstock is contacted in a reactor with a catalyst composition comprising at least two active catalytic components comprising, as a first active catalyst component, one or more materials selected from transition metals from groups 8, 9 or 10 or compounds thereof, with catalytic hydrogenation capabilities; and, as a second active catalyst component, one or more materials selected from tungsten, molybdenum and compounds and complexes thereof. The second active catalyst component may be present in homogeneous form.

Conversion of saccharides to glycols in the presence of a retro-aldol catalyst and a hydrogenation catalyst is highly sensitive to pH. In particular, in the absence of pH control, the pH of the reaction system decreases uncontrollably due to the formation of organic acids. Where the retro-aldol catalyst is a tungstate, the decrease in pH results in precipitation of the tungstate which is therefore detrimental to the process. In order to avoid or reduce such precipitation of catalyst, it is known to add one or more acids to buffer the reaction system.

WO 2015/154258 describes a process for converting saccharide-containing feedstock into ethylene glycol by contacting the feedstock with a two component catalyst system in the presence of hydrogen at a pH of from 2.0 to 6.5. The process is conducted in the presence of an organic or inorganic acid.

The present inventor has found that acids introduced into the process to act as buffers for maintaining the pH in the desired range are found in the water and glycol streams that are separated from the reactor product stream. Such contamination of the water and glycol product streams is undesirable since it necessitates additional processing to remove the acids from the product streams and further addition of acids to the reactor to maintain the desired buffering effect, hence increasing the cost of the glycol production.

It would therefore be advantageous to provide an improved process for pH control in the conversion of saccharides to glycols.

SUMMARY OF THE INVENTION

Accordingly, in one aspect, a process for the production of glycols is provided, the process comprising the steps of:
i) contacting a saccharide-containing feedstock with a catalyst system in a reactor in the presence of a reaction medium, a buffer system for controlling the pH within the reactor, and hydrogen;
ii) withdrawing a reactor product stream from the reactor;
iii) separating the reactor product stream into at least a glycol product stream and a hydrocarbon heavies stream; and
iv) recycling the hydrocarbon heavies stream at least partially back to the reactor; wherein components of the buffer system withdrawn from the reactor in the reactor product stream separate with the heavies stream and are recycled therewith.

By means of the invention in its first aspect, in addition to providing effective pH stabilisation in a desired pH range, the buffer system is primarily recycled via the hydrocarbon heavies stream and contamination of the glycol stream with buffer components is therefore avoided or at least substantially reduced. This is both economically and environmentally advantageous.

BRIEF DESCRIPTION OF THE DRAWINGS

FIG. 1 is a schematic representation of a process according to the invention.

DETAILED DESCRIPTION OF THE INVENTION

In the process of the present invention components of the buffer system are recycled with the hydrocarbon heavies stream, avoiding "contamination" of the glycol product stream. The term "hydrocarbon" as used herein covers not only chemical species that are composed only of hydrogen and carbon, but also to cover chemical species that are composed of hydrogen, carbon and oxygen. Oxygenates such as sugars, sugar alcohols, alcohols, diols and carboxylic acids are therefore considered to be "hydrocarbon" compounds for the purposes of the present invention.

In the present invention, the hydrocarbon heavies stream that is separated out from the reactor product stream along with the buffer components mainly comprises heavy hydrocarbon products that are formed in the glycol production process, e.g. the stream may comprise $C^{3+}$ sugar alcohols and carboxylic acids.

Components of the buffer system present in the heavies stream typically include metallic components, for example, alkaline metal components, such as sodium, as well as the conjugate base of the acid. In addition to components derived from the buffer system, the hydrocarbon heavies stream will typically also include other metallic components, such as those derived from the metallic homogeneous catalyst and/or a degradation product thereof that can result when such a metallic catalyst degrades.

The buffer system used in the process of the present invention preferably comprises a heavy organic acid. The term "heavy organic acid" used herein refers to an acid that remains in the liquid phase when water and $C_2$-$C_4$ glycols are boiled off the reactor product stream.

A buffer system comprising a heavy organic acid, being of lower volatility as compared to a volatile acid buffer such as one comprising sodium acetate/acetic acid, separates with the hydrocarbon heavies stream rather than with the glycol product stream thereby leaving the glycol product stream essentially free of buffer components. At the same time, use of heavy organic acids to maintain an acidic pH within the reactor is effective at optimising product glycol yield and reducing tungstate deposition.

Control of pH is preferably achieved using a buffer system comprising an organic acid with a pKa of from 3.0 to 4.5, more preferably from 3.5 to 4.0. Suitable buffer systems may comprise those based upon one or more of ascorbic acid, benzoic acid, oxalic acid, citric acid, adipic acid, lactic acid and/or glycolic acid.

Buffer systems based upon lactic acid and/or glycolic acid are especially advantageous since such components are also produced in the process of the invention. Thus, by basing the buffer system on lactic acid and/or glycolic acid it is possible to avoid introducing additional acid that is not naturally present in the reactor product stream to counter loss thereof during bleeding of the hydrocarbon heavies stream. Most preferably, the buffer system used in the process of the invention comprises sodium lactate/lactic acid and/or sodium glycolate/glycolic acid.

The buffer system is used to controlled the pH within a desired range. Preferably the buffer system in the reactor controls the pH within the range of 2.5 to 5, more preferably in the range of 2.5 to 4.5, most preferably in the range of 2.5 to 4.0.

In the process of the invention, the pH in the reactor may be controlled by adjusting the balance between the buffer acid and its conjugate base at a fixed buffer strength. For example, in relation to use of a 0.10 mol/l sodium glycolate/glycolic acid buffer system, the pH can be lowered by raising concentration of glycolic acid whilst reducing the concentration of sodium glycolate, as follows:

| Buffer Strength (mol/l) | pH (—) | NaGly (g/l) | HGly (g/l) |
|---|---|---|---|
| 0.10 | 2.6 | 0.302 | 7.418 |
| 0.10 | 2.8 | 0.687 | 7.120 |
| 0.10 | 3 | 1.174 | 6.743 |
| 0.10 | 3.2 | 1.812 | 6.248 |
| 0.10 | 3.4 | 2.634 | 5.610 |
| 0.10 | 3.6 | 3.633 | 4.836 |
| 0.10 | 3.8 | 4.748 | 3.971 |
| 0.10 | 4 | 5.878 | 3.095 |
| 0.10 | 4.2 | 6.911 | 2.293 |
| 0.10 | 4.4 | 7.772 | 1.626 |
| 0.10 | 4.6 | 8.433 | 1.113 |
| 0.10 | 4.8 | 8.912 | 0.742 |
| 0.10 | 5 | 9.243 | 0.485 |

Likewise, in relation to use of a 0.10 mol/l sodium lactate/lactic acid buffer system, the following concentrations may be used to adjust the pH:

| Buffer Strength (mol/l) | pH (—) | NaGly (g/l) | HGly (g/l) |
|---|---|---|---|
| 0.10 | 2.6 | 0.302 | 7.418 |
| 0.10 | 2.8 | 0.687 | 7.120 |
| 0.10 | 3 | 1.174 | 6.743 |
| 0.10 | 3.2 | 1.812 | 6.248 |
| 0.10 | 3.4 | 2.634 | 5.610 |
| 0.10 | 3.6 | 3.633 | 4.836 |
| 0.10 | 3.8 | 4.748 | 3.971 |
| 0.10 | 4 | 5.878 | 3.095 |
| 0.10 | 4.2 | 6.911 | 2.293 |
| 0.10 | 4.4 | 7.772 | 1.626 |
| 0.10 | 4.6 | 8.433 | 1.113 |
| 0.10 | 4.8 | 8.912 | 0.742 |
| 0.10 | 5 | 9.243 | 0.485 |

The amount of buffer supplied to the reactor is suitably from 0.05 to 5 wt % of buffer based on the total weight of feedstock supplied to the reactor, preferably from 0.1 to 2 wt % of buffer, more preferably from 0.7 to 1.0 wt % of buffer.

Suitable saccharide-containing feedstocks comprise at least one saccharide selected from the group consisting of monosaccharides, disaccharides, oligosaccharides, polysaccharides and a combination thereof. Examples of suitable polysaccharides include cellulose, hemicelluloses, starch, glycogen, chitin and any combination thereof. Examples of monosaccharides include glucose, fructose, etc. If the feedstock comprises oligosaccharides or polysaccharides, it is preferable that it is subjected to pre-treatment before being fed to a reactor in a form that can be converted in the processes of the present disclosure. Suitable pre-treatment methods are known in the art and include, but are not limited to, one or more of sizing, drying, blending, grinding, washing, de-watering, solids removal, steeping, milling, hot water treatment, steam treatment, hydrolysis (e.g. acid-catalysed hydrolysis, enzymatic hydrolysis), pyrolysis, thermal treatment, chemical treatment, biological treatment, purification, etc.

The saccharide feedstock used in the present invention may be derived from biomass, especially lignocellulosic biomass. Suitable saccharide-containing feedstocks may be obtained from grains such as corn, wheat, millet, oats, rye, sorghum, barley or buckwheat, from rice, from pulses such as soybean, pea, chickpea or lentil, from bananas and/or from root vegetables such as potato, yam, sweet potato, cassava and sugar beet, or any combinations thereof. A preferred source of a saccharide-containing feedstock is corn.

Preferably, a saccharide-containing feedstock supplied to a reactor after any optional pre-treatment comprises one or more saccharides selected from glucose, sucrose, and starch.

The saccharide-containing feedstock is generally supplied to a reactor in a reaction medium, preferably as a solution, a suspension or slurry in a solvent, or in one or more components of the solvent.

In a preferred embodiment, the reaction medium comprises a solvent comprising water and at least 25% by weight, based on the total weight of the solvent, of one or more alcohols selected from a $C_1$ to $C_6$ alcohol, a $C_1$ to $C_6$ polyalcohol, and a combination thereof. Saccharide-containing feedstock is more readily dissolved therein and thus, more readily hydrogenated, thereby minimising or preventing the fouling of one or more of the active catalytic components of the catalyst system.

Preferred $C_1$ to $C_6$ alcohols include methanol, ethanol, 1-propanol and iso-propanol. Polyalcohols of use include glycols, particularly products of the hydrogenation/hydrogenolysis reaction, glycerol, erythritol, threitol, sorbitol, 1,2-hexanediol and mixtures thereof. Preferably, a solvent comprises from 25% to 75% by weight, based on the total weight of the solvent, of the one or more alcohols and from 25% to 75% by weight, based on the total weight of the solvent, of water.

The solvent, or one or more of the components of the solvent (e.g. water and the one or more alcohols), may be added to the reactor in one or more separate feed streams. Similarly, the solvent, or one or more components thereof, may be added to the saccharide-containing feedstock before it enters the reactor.

The saccharide-containing feedstock is contacted with hydrogen in the presence of a catalyst system. Preferably the catalyst system comprises at least two active catalytic components, said active catalyst components comprising as a first active catalyst component, a retro-aldol catalyst, and as a second active catalyst component, a reducing catalyst.

The first active catalytic component, catalysing a retro-aldol reaction, preferably comprises one or more materials selected from tungsten, molybdenum, lanthanum, tin and compounds and complexes thereof. The second active catalyst component, catalysing reduction to the glycol preferably comprises one or more materials selected from transition metals from Groups 8, 9 or 10 or compounds thereof, with catalytic hydrogenation capabilities.

Preferably, the first active catalyst component comprises of one or more compound, complex or elemental material comprising tungsten, molybdenum, lanthanum or tin. More preferably, the first active catalyst component comprises one or more material selected from the list consisting of tungstic acid, molybdic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides and combinations thereof. The metal component is suitably in a form other than a carbide, nitride, or phosphide. Preferably, the second active catalyst component comprises one or more compound, complex or elemental material selected from those containing tungsten or molybdenum.

Preferably, the second active catalyst component consists of one or more of the group selected from iron, cobalt, nickel, ruthenium, rhodium, palladium, iridium and platinum. This component may be present in the elemental form or as a compound. It is also suitable that this component is present in chemical combination with one or more other ingredients in the catalyst system. It is required that the second active catalyst component has catalytic hydrogenation capabilities and it is capable of catalysing the hydrogenation of material present in the reactor.

The catalyst system and the components contained therein may be heterogeneous or homogeneous with respect to the solvent or solvents present in the reactor. The catalyst composition may also contain both heterogeneous and homogeneous components.

Depending on the physical state of the catalyst composition and any components contained therein, they may be preloaded into the reactor or, if they are in liquid form or present as a solution or slurry in a solvent, they may be fed into the reactor as required in a continuous or discontinuous manner.

Preferably, one or both of the active catalyst components is supported on a solid support. In one embodiment of the invention, the first active catalyst component is supported on one solid support and the second active catalyst component is supported on a second solid support which may comprise the same or different material. In another embodiment, both active catalyst components are supported on one solid support.

The solid supports may be in the form of a powder or in the form of regular or irregular shapes such as spheres, extrudates, pills, pellets, tablets, monolithic structures. Alternatively, the solid supports may be present as surface coatings, for example on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

Suitably, the weight ratio of the second active catalyst component to the first active catalyst component is in the range of from 0.02:1 to 3000:1, preferably in the range of from 0.1:1 to 100:1, on the basis of the weight of metal present in each component.

The weight ratio of the first active catalyst component (based on the amount of metal in said component) to sugar is suitably in the range of from 1:10 to 1:100. The weight ratio of the second active catalyst component (based on the amount of metal in said component) to sugar is suitably in the range of from 1:100 to 1:1000.

The saccharide-containing feedstock may be contacted sequentially with the first active component and the second active component, for example, in different zones of a single reactor, or in a series of reactors. In practice, several reactors may be employed, arranged in series or in parallel. For simplicity, the term "reactor" used herein embraces both single and multiple reactors, whether in series or parallel. Where multiple reactors are used, it is preferred that the same buffer system is used throughout. Buffer strength may however differ between reactors.

In one embodiment, the composition of the catalyst system changes across the length of the reactor, for example, the content of retro-aldol catalyst reduces and the content of reducing catalyst increases between the input and output ends of the reactor.

Alternatively, separate catalysis zones may be provided by means of separate reactors, thereby facilitating use of different operating temperatures as the reaction progresses.

If more than one reactor is used in series, a catalyst composition may optionally be present in the second and any subsequent reactors. If a catalyst composition is present in the second and any subsequent reactor, the catalyst composition used in each of the reactors may be the same or different. Additionally, the weight ratio of the active catalyst components may be varied between the first and second reactors (and any subsequent reactors) and it may be advantageous to alter the composition of the catalyst systems between the reactors to suit the different feed streams provided to each reactor. Suitably, reaction conditions, particularly temperature and pressure, can be varied between the reactors if more than one reactor is used. This can lead to a more tailored process to suit the different constituents of the feeds provided to each reactor.

The reaction temperature at which the saccharide-containing feedstock is contacted with hydrogen in the presence of the catalyst composition described herein is suitably at least 130° C., preferably at least 150° C., more preferably at least 170° C., most preferably at least 190° C. The temperature in the reactor is suitably at most 300° C., preferably at most 280° C., more preferably at most 270° C., even more preferably at most 250° C. Preferably, the reactor is heated to a temperature within these limits before addition of the saccharide-containing feedstock and is maintained at such a temperature as the reaction proceeds.

The pressure in the reactor or reactors in which the saccharide-containing feedstock is contacted with hydrogen in the presence of the catalyst composition described herein is suitably at least 1 MPa, preferably at least 2 MPa, more preferably at least 3 MPa. The pressure in the reactor is suitably at most 15 MPa, preferably at most 12 MPa, more preferably at most 10 MPa, most preferably at most 8 MPa. Preferably, the reactor is pressurised to a pressure within these limits by addition of hydrogen before addition of any saccharide-containing feedstock and is maintained at such a pressure as the reaction proceeds through on-going addition of hydrogen.

The process of the present disclosure takes place in the presence of hydrogen. Preferably, the processes take place in the absence of air or oxygen. In order to achieve this, it is preferable that the atmosphere in the reactor be evacuated and replaced an inert gas, such as nitrogen, and then with hydrogen repeatedly, after loading of any initial reactor contents, before the reaction starts.

Suitable reactors include stirred tank reactors, slurry reactors, ebulated bed reactors, jet flow reactors, mechanically agitated reactors, bubble columns, such as slurry bubble columns and external recycle loop reactors. The use of these reactors allows dilution of the saccharide-containing feedstock and intermediates to an extent that provides high degrees of selectivity to the desired glycol product (mainly ethylene and propylene glycols), such as by effective back-mixing.

The residence time in the reactor is suitably at least 1 minute, preferably at least 2 minutes, more preferably at least 5 minutes. Suitably the residence time in the reactor is no more than 5 hours, preferably no more than 2 hours, more preferably no more than 1 hour.

In the process of the invention, a reactor product stream is withdrawn from the reactor. Typically this stream contains water, hydrocarbons, homogeneous catalyst and buffer. The reactor product stream is separated into at least a glycol product stream and a hydrocarbon heavies stream. The reactor product stream may additionally be separated into a light hydrocarbon stream and water. In a preferred separation step, the light hydrocarbon stream is first separated from the reactor product stream and then the water is removed by distillation. The glycol product stream is then separated from the hydrocarbon heavies stream by distillation (the hydrocarbon heavies stream is the bottom product from this distillation).

The glycol product stream typically comprises as least one of monoethylene glycol (MEG), monopropylene glycol (MPG) and 1,2-butanediol (1,2-BDO). The different glycols may be collected as separate streams or as one combined stream.

A hydrocarbon heavies stream is separated from the reactor product stream, and is at least partially recycled back to the reactor, either directly or indirectly. The hydrocarbon heavies stream contains heavy hydrocarbons and the buffer components. Components of the catalyst system may also be present in the hydrocarbon heavies stream. Accordingly, the recycling of this stream enables reuse of the catalyst components, as well as recycling of buffer components.

A hydrocarbon product stream may be bled from the hydrocarbon heavies stream as it is recycled to the reactor. In this context, "bleeding" means removing small quantities of material from the recycle on a regular basis. Suitably from 1 to 20 wt % and preferably around 10 wt % of the hydrocarbon heavies stream is bled to provide the hydrocarbon product stream. This is suitably done on a continuous basis by splitting the hydrocarbon heavies stream into a minor stream (which becomes the hydrocarbon product stream) and a major stream (which is recycled to the reactor).

The hydrocarbon product stream may be subjected to a thermal oxidation, typically at a temperature of from 300 to 750° C., to provide a solid residue. The solid residue may be collected in solid form, or it may be dissolved in a solvent, thereby providing a solution that can be subjected to further processing.

Having generally described the invention, a further understanding may be obtained by reference to the following example, which is provided for purposes of illustration and is not intended to be limiting unless otherwise specified.

FIG. 1 shows an example of a process according to the invention wherein glycols are prepared from a saccharide-containing feedstock. A saccharide-containing feedstock, water, hydrogen, a catalyst system and a heavy organic acid buffer system are fed (1) to a reactor (2). The reactor (2) contains two active catalytic components, specifically a heterogeneous hydrogenation catalyst and a homogeneous retro-aldol catalyst. The saccharide-containing feedstock reacts to provide glycols. A reactor product stream (3) from the reactor (2) is provided to a separator (4). Water (5) is withdrawn from the separator (4). A glycols product stream (6) is withdrawn from the separator (4). A hydrocarbon heavies stream (7) also containing components of the buffer system is withdrawn from the separator (4) and is recycled to the reactor (2). A hydrocarbon product stream (8) is bled from the hydrocarbon heavies stream (7) and is supplied to an oven (9). In the oven (9) the hydrocarbon product stream (8) is subjected to a thermal oxidation at a temperature of from 300 to 750° C. A solid residue is collected from the oven (9).

That which is claimed is:

1. A process for the production of glycols comprising the steps of:
    (i) contacting a saccharide-containing feedstock with a catalyst system in a reactor in the presence of a reaction medium, a buffer system for controlling the pH within the reactor, and hydrogen;
    (ii) withdrawing a reactor product stream from the reactor;
    (iii) separating the reactor product stream into at least a glycol product stream and a hydrocarbon heavies stream; and
    (iv) recycling the hydrocarbon heavies stream at least partially back to the reactor;
    wherein components of the buffer system withdrawn from the reactor in the reactor product stream separate with the heavies stream and are recycled therewith.

2. The process as claimed in claim 1, wherein the buffer system comprises a heavy organic acid.

3. The process as claimed in claim 1, wherein the buffer system comprises an organic acid with a pKa of from 3.0 to 4.5.

4. The process as claimed in claim 3, wherein the buffer system comprises sodium lactate/lactic acid and/or sodium glycolate/glycolic acid.

5. The process as claimed in claim 1, wherein buffer system in the reactor controls the pH within the range of 2.5 to 5.

6. The process as claimed in claim 1, wherein the catalyst system comprises a first active catalytic component comprising one or more materials selected from tungsten, molybdenum, lanthanum, tin and compounds and complexes thereof and a second active catalyst component comprising one or more materials selected from transition metals from Groups 8, 9 or 10 or compounds thereof, with catalytic hydrogenation capabilities.

7. The process as claimed in claim 6, wherein the first active catalyst component comprises one or more materials selected from the list consisting of tungstic acid, molybdic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides and combinations thereof, and the second active catalyst component comprises of one or more of the group selected from iron, cobalt, nickel, ruthenium, rhodium, palladium, iridium and platinum.

8. The process as claimed in claim 1 comprising multiple reactors, wherein the buffer strength differs between reactors.

9. The process as claimed in claim 1, wherein the amount of buffer supplied to the reactor is from 0.05 to 5 wt % based on the total weight of feedstock supplied to the reactor.

10. The process as claimed in claim 1, wherein the glycols comprise monoethylene and monopropylene glycols.

* * * * *